United States Patent [19]

Suzuki et al.

[11] Patent Number: 5,808,031
[45] Date of Patent: Sep. 15, 1998

[54] GRP17 GENE

[75] Inventors: Mikio Suzuki, Tokushima; Takeshi Watanabe, Tokushima-ken; Tsutomu Fujiwara, Naruto, all of Japan

[73] Assignee: Otsuka Pharmaceutical Co., Ltd., Tokyo, Japan

[21] Appl. No.: 797,831

[22] Filed: Feb. 10, 1997

[30] Foreign Application Priority Data

Feb. 9, 1996 [JP] Japan .................................. 8-023612

[51] Int. Cl.$^6$ ........................... C07H 21/04; C07K 14/47
[52] U.S. Cl. .......................................... 536/23.5; 530/350
[58] Field of Search ............................ 536/23.5; 530/350

[56] References Cited

PUBLICATIONS

Abdollahi A; Lord K A; Hoffman–Liebermann B; Liebermann D A. Sequence and expression of a cDNA encoding MyD118: a novel myeloid differentiation primary response gene induced by multiple cytokines. ONCOGENE, (1991 Jan.), 6 (1) 165–7.

Papathanasiou M A; Kerr N C; Robbins J H; McBride O W; Alamo I Jr; Barrett S F; Hickson I D; Fornace A J Jr. Induction by ionizing radiation of the gadd45 gene in cultured human cells: lack of mediation by protein kinase C. Molecular and Cellular Biology, (1991 Feb.), 11(2), 1009–1016.

Carrier et al., J. Biol. Chem., vol. 269, No. 51, 23672–23677 (1994).

*Primary Examiner*—Elizabeth C. Kemmerer
*Assistant Examiner*—David S. Romeo
*Attorney, Agent, or Firm*—Sughrue, Mion, Zinn, Macpeak & Seas, PLLC

[57] ABSTRACT

The present invention provides a human GRP17 gene which comprises a nucleotide sequence coding for the amino acid sequence of SEQ ID NO:1. The gene can be used in the expression and detection of the GRP17 protein and in the diagnosis of various diseases in which the protein is involved, pathological studies of such diseases, and screening out and evaluation of drugs for the treatment and prevention of such diseases.

3 Claims, 1 Drawing Sheet

FIG. 1

| | | 10 | 20 | 30 | 40 | 50 |
|---|---|---|---|---|---|---|
| hGRP17 | 1 | MTLEEVRGQD | TVPESTARMQ | GAGKALHELL | LSAHGQGCLT | AGVYESAKLM |
| hGADD45 | 1 | MTLEEFSAGE | ---QKTERMD | KVGDALEEML | SKALSQRTIT | VGVYEAAKLL |
| mMyD | 1 | MTLEELVASD | ---NAVQKMQ | AMFAAVEQLL | VAAQRQDRLT | VGVYEAAKLM |

| | | 60 | 70 | 80 | 90 | 100 |
|---|---|---|---|---|---|---|
| hGRP17 | 51 | NVDPDNVTFC | VLAAGEEDEG | DIALQIHFTL | IQAFCCENDI | DIVRVGDVQR |
| hGADD45 | 51 | NVDPDNVVLC | LLAADEDDDR | DVALQIHFTL | IQAFCCENDI | NILRVSNPGR |
| mMyD | 51 | NVDPDSVVLC | LLATDEEEED | DIALQIHFTL | IQSFCCDNDI | DIVRVSGMQR |

| | | 110 | 120 | 130 | 140 | 150 |
|---|---|---|---|---|---|---|
| hGRP17 | 101 | LAAIV---- | ---GAGEEAG | APGDLHCILL | SNPNEDAWKD | PALEKLSLFC |
| hGADD45 | 101 | LAELLLLETD | AGPAASEGAE | QPPDLHCMLV | TNPHSSQWKD | PALSQLICEC |
| mMyD | 101 | LAQLL---- | GEPAFTLGTT | EARDLHCQLV | TNCHTDSWKS | QGLVEVASYC |

| | | 160 | | | | |
|---|---|---|---|---|---|---|
| hGRP17 | 151 | EESRSVNDWV | PSITLPE-- | | | |
| hGADD45 | 151 | RESRYMDQWV | PVINLPER- | | | |
| mMyD | 151 | EESRGNNQWV | PYISLEER- | | | |

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 159 amino acids
( B ) TYPE: amino acid
( C ) STRANDEDNESS:
( D ) TOPOLOGY: linear ( i i ) MOLECULE TYPE: protein ( x i ) SEQUENCE DESCRIPTION: SEQ ID NO:1:

```
Met Thr Leu Glu Glu Val Arg Gly Gln Asp Thr Val Pro Glu Ser Thr
  1               5                  10                  15

Ala Arg Met Gln Gly Ala Gly Lys Ala Leu His Glu Leu Leu Leu Ser
             20                  25                  30

Ala His Gly Gln Gly Cys Leu Thr Ala Gly Val Tyr Glu Ser Ala Lys
         35                  40                  45

Val Leu Asn Val Asp Pro Asp Asn Val Thr Phe Cys Val Leu Ala Ala
     50                  55                  60

Gly Glu Glu Asp Glu Gly Asp Ile Ala Leu Gln Ile His Phe Thr Leu
 65                  70                  75                  80

Ile Gln Ala Phe Cys Cys Glu Asn Asp Ile Asp Ile Val Arg Val Gly
                 85                  90                  95

Asp Val Gln Arg Leu Ala Ala Ile Val Gly Ala Gly Glu Glu Ala Gly
                100                 105                 110

Ala Pro Gly Asp Leu His Cys Ile Leu Ile Ser Asn Pro Asn Glu Asp
            115                 120                 125
```

```
      Ala  Trp  Lys  Asp  Pro  Ala  Leu  Glu  Lys  Leu  Ser  Leu  Phe  Cys  Glu  Glu
           130                      135                      140

Ser  Arg  Ser  Val  Asn  Asp  Trp  Val  Pro  Ser  Ile  Thr  Leu  Pro  Glu
      145                      150                      155
```

( 2 ) INFORMATION FOR SEQ ID NO:2:

( i ) SEQUENCE CHARACTERISTICS:
        ( A ) LENGTH: 477 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

```
ATGACTCTGG  AAGAAGTCCG  CGGCCAGGAC  ACAGTTCCGG  AAAGCACAGC  CAGGATGCAG      60

GGTGCCGGGA  AAGCGCTGCA  TGAGTTGCTG  CTGTCGGCGC  ACGGTCAGGG  CTGCCTCACT     120

GCCGGCGTCT  ACGAGTCAGC  CAAAGTCTTG  AACGTGGACC  CCGACAATGT  GACCTTCTGT     180

GTGCTGGCTG  CGGGTGAGGA  GGACGAGGGC  GACATCGCGC  TGCAGATCCA  TTTTACGCTG     240

ATCCAGGCTT  TCTGCTGCGA  GAACGACATC  GACATAGTGC  GCGTGGGCGA  TGTGCAGCGG     300

CTGGCGGCTA  TCGTGGGCGC  CGGCGAGGAG  GCGGGTGCGC  CGGGCGACCT  GCACTGCATC     360

CTCATTTCGA  ACCCCAACGA  GGACGCCTGG  AAGGATCCCG  CCTTGGAGAA  GCTCAGCCTG     420

TTTTGCGAGG  AGAGCCGCAG  CGTTAACGAC  TGGGTGCCCA  GCATCACCCT  CCCCGAG        477
```

( 2 ) INFORMATION FOR SEQ ID NO:3:

( i ) SEQUENCE CHARACTERISTICS:
        ( A ) LENGTH: 1036 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 84..560

( x i ) SEQUENCE DESCRIPTION: SEQ ID NO:3:

```
CTGAGCTCTG  GCTGTCAGTG  TGTTCGCCCG  CGTCCCCTCC  GCGCTCTCCG  CTTGTGGATA         60

ACTAGCTGCT  GGTTGATCGC  ACT ATG ACT CTG GAA GAA GTC CGC GGC CAG                110
                           Met Thr Leu Glu Glu Val Arg Gly Gln
                            1               5

GAC ACA GTT CCG GAA AGC ACA GCC AGG ATG CAG GGT GCC GGG AAA GCG                158
Asp Thr Val Pro Glu Ser Thr Ala Arg Met Gln Gly Ala Gly Lys Ala
 10              15                  20                      25

CTG CAT GAG TTG CTG CTG TCG GCG CAC GGT CAG GGC TGC CTC ACT GCC                206
Leu His Glu Leu Leu Leu Ser Ala His Gly Gln Gly Cys Leu Thr Ala
                 30                  35                  40

GGC GTC TAC GAG TCA GCC AAA GTC TTG AAC GTG GAC CCC GAC AAT GTG                254
Gly Val Tyr Glu Ser Ala Lys Val Leu Asn Val Asp Pro Asp Asn Val
             45                  50                  55

ACC TTC TGT GTG CTG GCT GCG GGT GAG GAG GAC GAG GGC GAC ATC GCG                302
Thr Phe Cys Val Leu Ala Ala Gly Glu Glu Asp Glu Gly Asp Ile Ala
             60                  65                  70
```

```
CTG  CAG  ATC  CAT  TTT  ACG  CTG  ATC  CAG  GCT  TTC  TGC  TGC  GAG  AAC  GAC        350
Leu  Gln  Ile  His  Phe  Thr  Leu  Ile  Gln  Ala  Phe  Cys  Cys  Glu  Asn  Asp
     75                       80                       85

ATC  GAC  ATA  GTG  CGC  GTG  GGC  GAT  GTG  CAG  CGG  CTG  GCG  GCT  ATC  GTG        398
Ile  Asp  Ile  Val  Arg  Val  Gly  Asp  Val  Gln  Arg  Leu  Ala  Ala  Ile  Val
90                            95                       100                 105

GGC  GCC  GGC  GAG  GAG  GCG  GGT  GCG  CCG  GGC  GAC  CTG  CAC  TGC  ATC  CTC        446
Gly  Ala  Gly  Glu  Glu  Ala  Gly  Ala  Pro  Gly  Asp  Leu  His  Cys  Ile  Leu
                    110                      115                      120

ATT  TCG  AAC  CCC  AAC  GAG  GAC  GCC  TGG  AAG  GAT  CCC  GCC  TTG  GAG  AAG        494
Ile  Ser  Asn  Pro  Asn  Glu  Asp  Ala  Trp  Lys  Asp  Pro  Ala  Leu  Glu  Lys
               125                      130                      135

CTC  AGC  CTG  TTT  TGC  GAG  GAG  AGC  CGC  AGC  GTT  AAC  GAC  TGG  GTG  CCC        542
Leu  Ser  Leu  Phe  Cys  Glu  Glu  Ser  Arg  Ser  Val  Asn  Asp  Trp  Val  Pro
          140                      145                      150

AGC  ATC  ACC  CTC  CCC  GAG  TGACAGCCCG  GCGGGGACCT  TGGTCTGATC                       590
Ser  Ile  Thr  Leu  Pro  Glu
          155
```

GACGTGGTGA CGCCCCGGGG CGCCTAGAGC GCGGCTGGCT CTGTGGAGGG GCCCTCCGAG        650

GGTGCCCGAG TGCGGCGTGG AGACTGGCAG GCGGGGGGGG CGCCTGGAGA GCGAGGAGGC        710

GCGGCCTCCC GAGGAGGGGC CCGGTGGCGG CAGGGCCAGG CTGGTCCGAG CTGAGGACTC        770

TGCAAGTGTC TGGAGCGGCT GCTCGCCCAG GAAGGCCTAG GCTAGGACGT TGGCCTCAGG        830

GCCAGGAAGG ACAGACTGGC CGGGCAGGCG TGACTCAGCA GCCTGCGCTC GGCAGGAAGG        890

AGCGGCGCCC TGGACTTGGT ACAGTTGCAG GAGCGTGAAG GACTTAGCCG ACTGCGCTGC        950

TTTTTCAAAA CGGATCCGGG CAATGCTTCG TTTTCTAAAG GATGCTGCTG TTGAAGCTTT       1010

GAATTTTACA ATAAACTTTT TGAAAC                                             1036

( 2 ) INFORMATION FOR SEQ ID NO:4:

( i ) SEQUENCE CHARACTERISTICS:
        ( A ) LENGTH: 159 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Thr  Leu  Glu  Glu  Val  Arg  Gly  Gln  Asp  Thr  Val  Pro  Glu  Ser  Thr
1                   5                        10                      15

Ala  Arg  Met  Gln  Gly  Ala  Gly  Lys  Ala  Leu  His  Glu  Leu  Leu  Leu  Ser
               20                       25                      30

Ala  His  Gly  Gln  Gly  Cys  Leu  Thr  Ala  Gly  Val  Tyr  Glu  Ser  Ala  Lys
          35                       40                      45

Val  Leu  Asn  Val  Asp  Pro  Asp  Asn  Val  Thr  Phe  Cys  Val  Leu  Ala  Ala
     50                       55                      60

Gly  Glu  Glu  Asp  Glu  Gly  Asp  Ile  Ala  Leu  Gln  Ile  His  Phe  Thr  Leu
65                       70                      75                       80

Ile  Gln  Ala  Phe  Cys  Cys  Glu  Asn  Asp  Ile  Asp  Ile  Val  Arg  Val  Gly
               85                       90                      95

Asp  Val  Gln  Arg  Leu  Ala  Ala  Ile  Val  Gly  Ala  Gly  Glu  Glu  Ala  Gly
               100                      105                     110

Ala  Pro  Gly  Asp  Leu  His  Cys  Ile  Leu  Ile  Ser  Asn  Pro  Asn  Glu  Asp
          115                      120                     125

Ala  Trp  Lys  Asp  Pro  Ala  Leu  Glu  Lys  Leu  Ser  Leu  Phe  Cys  Glu  Glu
     130                      135                     140
```

Ser Arg Ser Val Asn Asp Trp Val Pro Ser Ile Thr Leu Pro Glu
145                 150                 155

(2) INFORMATION FOR SEQ ID NO:5:

(i) SEQUENCE CHARACTERISTICS:
        (A) LENGTH: 165 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:5:

Met Thr Leu Glu Glu Phe Ser Ala Gly Glu Gln Lys Thr Glu Arg Met
1               5                   10                  15

Asp Lys Val Gly Asp Ala Leu Glu Glu Val Leu Ser Lys Ala Leu Ser
                20                  25                  30

Gln Arg Thr Ile Thr Val Gly Val Tyr Glu Ala Ala Lys Leu Leu Asn
            35                  40                  45

Val Asp Pro Asp Asn Val Val Leu Cys Leu Leu Ala Ala Asp Glu Asp
        50                  55                  60

Asp Asp Arg Asp Val Ala Leu Gln Ile His Phe Thr Leu Ile Gln Ala
65                  70                  75                  80

Phe Cys Cys Glu Asn Asp Ile Asn Ile Leu Arg Val Ser Asn Pro Gly
                85                  90                  95

Arg Leu Ala Glu Leu Leu Leu Leu Glu Thr Asp Ala Gly Pro Ala Ala
                100                 105                 110

Ser Glu Gly Ala Glu Gln Pro Pro Asp Leu His Cys Val Leu Val Thr
            115                 120                 125

Asn Pro His Ser Ser Gln Trp Lys Asp Pro Ala Leu Ser Gln Leu Ile
        130                 135                 140

Cys Phe Cys Arg Glu Ser Arg Tyr Met Asp Gln Trp Val Pro Val Ile
145                 150                 155                 160

Asn Leu Pro Glu Arg
                165

(2) INFORMATION FOR SEQ ID NO:6:

(i) SEQUENCE CHARACTERISTICS:
        (A) LENGTH: 160 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:6:

Met Thr Leu Glu Glu Leu Val Ala Ser Asp Asn Ala Val Gln Lys Met
1               5                   10                  15

Gln Ala Val Thr Ala Ala Val Glu Gln Leu Leu Val Ala Ala Gln Arg
                20                  25                  30

Gln Asp Arg Leu Thr Val Gly Val Tyr Glu Ala Ala Lys Leu Met Asn
            35                  40                  45

Val Asp Pro Asp Ser Val Val Leu Cys Leu Leu Ala Ile Asp Glu Glu
        50                  55                  60

Glu Glu Asp Asp Ile Ala Leu Gln Ile His Phe Thr Leu Ile Gln Ser
65                  70                  75                  80

Phe Cys Cys Asp Asn Asp Ile Asp Ile Val Arg Val Ser Gly Met Gln
                85                  90                  95

```
    Arg  Leu  Ala  Gln  Leu  Leu  Gly  Glu  Pro  Ala  Glu  Thr  Leu  Gly  Thr  Thr
                   100                      105                      110

Glu  Ala  Arg  Asp  Leu  His  Cys  Leu  Leu  Val  Thr  Asn  Cys  His  Thr  Asp
                   115                      120                      125

Ser  Trp  Lys  Ser  Gln  Gly  Leu  Val  Glu  Val  Ala  Ser  Tyr  Cys  Glu  Glu
         130                      135                      140

Ser  Arg  Gly  Asn  Asn  Gln  Trp  Val  Pro  Tyr  Ile  Ser  Leu  Glu  Glu  Arg
    145                      150                      155                      160
```

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:7:

```
TAGGCTAGGA CGTTGCCTCA                                                          20
```

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:8:

```
GCTTCAACAG CAGCATCCTT                                                          20
```

GRP17 GENE

TECHNICAL FIELD

The present invention relates to a human gene which is associated with arrest of cell growth and DNA damage induction and is useful for the diagnosis and treatment of cancer. More particularly, it relates to a novel gene designated as human GRP17 (gadd45 and MyD118 related protein, 17 kDa) gene, which encodes a protein highly homologous to the proteins encoded by the Gadd45 gene and MyD118 gene.

BACKGROUND ART

Growth arrest and apoptosis are important for the regulation of cell growth. A remarkable relation is observed between the gadd genes, a set of genes capable of inducing growth arrest and DNA damage [Fornace, A. J., et al., Mol. Cell. Biol., 9, 4196–4203 (1989)], and the MyD genes, a set of myeloid differentiation primary response genes [Lord, K. A., et al., Oncogene, 5, 387–396 (1990)]. Thus, among these gene groups, gadd34/MyD116, gadd45, MyD118 and gadd153 have multiple common properties, such as roles in growth control, acidic amino acid clusters, similarities in expression and regulation pattern. These gene groups may define a novel gene family encoding acidic proteins that synergistically suppress cell growth [Zhan, Q., et al., Mol. Cell. Biol., 14, 2361–2371 (1994)]. However, the mechanisms of cell growth control by them still mostly remain unknown.

Gadd45 [Carrier, F., et al., J. Biol. Chem., 269, 32672–32677 (1994)] and MyD118 [Abdollahi, A., et al., Oncogene, 6, 165–167 (1991)] are very similar in DNA sequence although they are two distinct genes.

Expression of gadd45 is induced by a wide variety of stresses, and regulated by p53 [Hollander, M. C., et al., J. Biol. Chem., 268, 24385–24393 (1993)].

Recently, Smith et al. have reported that gadd45 binds to PCNA (proliferating cell nuclear antigen) and stimulates DNA excision repair [Smith, M. L., et al., Science, 266, 1376–1380 (1994)]. Furthermore, it has been also reported that gadd45 interacts with $p21^{waf1/cip1}$ (cyclin-dependent kinase inhibitor) and modulates the cell cycle for inhibition of DNA replication, suggesting that gadd45 may play an important role in cell cycle regulation [Chen, I. T., et al., Oncogene, 11, 1931–1937 (1995); Kearsey, J. M., et al., Oncogene, 11, 1675–1683 (1995)].

If a human gene coding for a protein highly homologous to the above-mentioned gadd45 and MyD118, it will be possible to analyze the level of expression thereof in each kind of cells and the structure and function thereof and, through expression product analysis and other studies, it may become possible to reveal the pathogenesis of a disease associated therewith, for example cancer, or diagnose and treat said disease, for instance. No report has so far been made on such gene, however.

It is an object of the present invention to provide such a novel human gene capable of growth arrest and DNA damage induction.

DISCLOSURE OF THE INVENTION

The present inventors made intensive investigations to accomplish the above object and, as a result, successfully isolated, from a human cDNA library, a new gene which answers the above object. This has led to completion of the present invention.

Thus, the present invention provides a gene comprising a nucleotide sequence coding for the amino acid sequence of SEQ ID NO:1 (such gene is hereinafter referred to as "GRP17 gene") and, more particularly, a GRP17 gene comprising the nucleotide sequence of SEQ ID NO:2 and a GRP17 gene having the nucleotide sequence of SEQ ID NO:3.

The symbols used herein for indicating amino acids, peptides, nucleotide sequences, nucleic acids and so on are those recommended by IUPAC and IUB or in "Guide line for drafting specifications etc. including nucleotide sequences or amino acid sequences" (edited by the Japanese Patent Office), or those in conventional use in the relevant fields of art.

As typical examples of the GRP17 gene of the present invention, there may be mentioned those which are deduced from the DNA sequence of the clone designated "GEN-554H06" as mentioned later herein in an example. Said clone has an open reading frame composed of the 477 nucleotides (nucleic acid) shown in SEQ ID NO:2 and encoding the 159 amino acid residues shown in SEQ ID NO:1.

The estimable molecular weight of the protein encoded by the gene of the present invention is calculated at 17,030 daltons. Northern blot analysis revealed strong expression of a 1.35 Kb (kilo bases) transcript in the following tissues among the human adult tissues examined: heart, pancreas, liver, skeletal muscle, prostate gland, testis and ovary. In addition, another transcript, namely a 1.7 Kb transcript, was also detected in liver. Furthermore, the gene of the present invention was mapped on the chromosomal band 9q22.1–q22.2.

So far, nothing was known about the function or intracellular localization of GRP17. These have now been revealed by the present invention and, furthermore, it has been revealed that the above-mentioned GRP17 gene is tissue-specific.

Since the gene of the present invention is supposedly involved in cell cycle suppression, it is considered that this gene product is a factor associated with cell growth suppression control or with canceration. It is thought that this gene, when it is abnormal, may possibly induce cancer or malformation and that said gene can be applied clinically in the diagnosis of cancer and/or the treatment of cancer, malformation, etc.

In addition, the gene of the present invention is involved in apoptosis and a wide range of application thereof not only in cell cycle suppression but also in the field of therapy can be expected.

In the following, the GRP17 gene of the present invention is described in further detail.

As mentioned hereinabove, it is already known that gadd45 and MyD118 are involved in cell growth control and that they constitute an acidic protein-encoding gene family and synergistically suppress cell growth. These genes are supposed to function as tumor suppression associated genes.

The GRP17 gene of the present invention is highly homologous to the above-mentioned gadd45 and MyD118. Thus, on the amino acid level, the deduced human GRP17 protein is 55% and 52% identical with gadd45 and MyD118, respectively, indicating high levels of homology.

The gene of the present invention is represented in a single-stranded DNA sequence, as shown in SEQ ID NO:2. It is to be noted, however, that the present invention also includes a DNA sequence complementary to such a single-stranded DNA sequence and thus emcompasses a component comprising both. The sequence of the gene of the present invention, in SEQ ID NO:2, is merely an example of the possible combination of codons encoding the respective amino acid residues. The gene of the present invention is not limited thereto but can of course have a DNA base sequence in which the codons are arbitrarily selected for the respective amino acid residues for combination. The codon selection can be made in the conventional manner, for example based on the codon frequency pattern in the host employed [Nucl. Acids Res., 9, 43–74 (1981)).

The gene of the present invention further includes DNA sequences coding for functional equivalents derived from the amino acid sequence mentioned above by partial amino acid or amino acid sequence substitution, deletion or addition. These polypeptides may be produced by spontaneous modification (mutation) or may be obtained by posttranslational modification or by modifying the natural gene (of the present invention) by a technique of genetic engineering, for example by site-specific mutagenesis [Methods in Enzymology, 154, p. 350, 367–382 (1987); ibid., 100, p. 468 (1983); Nucleic Acids Research, 12, p. 9441 (1984); Zoku Seikagaku Jikken Koza (Sequel to Experiments in Biochemistry) 1, "Idensi Kenkyu-ho (Methods in Gene Research) II", edited by the Japan Biochemical Society, p. 105 (1986)] or synthesizing mutant DNAs by a chemical synthetic technique such as the phosphotriester method or phosphoamidite method [J. Am. Chem. Soc., 89, p. 4801 (1967); ibid., 91, p. 3350 (1969); Science, 150, p. 178 (1968); Tetrahedron Lett., 22, p. 1859 (1981); ibid., 24, p. 245 (1983)], or by using a combination of the techniques mentioned above.

The GRP17 protein mentioned above can be expressed readily and stably by utilizing the gene of the present invention, for example inserting it into a vector for use with a microorganism and cultivating the microorganism thus transformed.

The GRP17 protein obtained by utilizing the gene of the present invention can be used in specific antibody production. In this case, the protein producible in large quantities by the technology of genetic engineering mentioned above can be used as the component to serve as an antigen. The antibody obtained may be polyclonal or monoclonal and can be advantageously used in the purification, assay, discrimination or identification of the GRP17 protein.

The gene of the present invention can be readily produced based on the sequence information thereof disclosed herein by using general genetic engineering techniques [cf. e.g. Molecular Cloning, 2nd Ed., Cold Spring Harbor Laboratory Press (1989); Zoku Seuikagaku Jikken Koza, "Idenshi Kenkyu-ho I, II and III", edited by the Japan Biochemical Society (1986)].

This can be realized, for example, by selecting a desired clone from a human cDNA library (prepared in the conventional manner from appropriate cells of origin in which the GRP17 gene is expressed) using a probe or antibody specific to the gene of the present invention [e.g. Proc. Natl. Acad. Sci. USA, 78, 6613 (1981); Science, 222, 778 (1983)].

The cells of origin to be used in the above method are, for example, cells or tissues of various kinds in which the GRP17 gene is expressed, or cultured cells derived therefrom. Separation of total RNA, separation and purification of mRNA, conversion to (synthesis of) cDNA, cloning thereof and so on can be carried out by conventional methods. cDNA libraries are also commercially available and such cDNA libraries, for example various cDNA libraries available from Clontech Lab. Inc. can also be used in the practice of the present invention.

Screening of a cDNA library for the gene of the present invention can be carried out by the conventional method mentioned above. As said method of screening, there may be mentioned, for example, the method comprising selecting a corresponding cDNA clone by immunological screening using a GRP17-specific antibody against proteins produced by cDNA, the technique of plaque hybridization or colony hybridization using a probe selectively binding to the desired DNA sequence, or a combination of these. As regards the probe to be used here, a DNA sequence chemically synthesized based on the information about the DNA sequence of the present invention is generally used. It is of course possible to use, as such probe, the gene of the present invention as already obtained or a fragment thereof.

For obtaining the gene of the present invention, the technique of DNA/RNA amplification by the PCR method [Science, 230, 1350–1354 (1985)] can suitably be employed. Particularly when the full-length cDNA can hardly be obtained from the library, the RACE method [rapid amplification of cDNA ends; Jikken Igaku (Experimental Medicine), 12 (6), 35–38 (1994)], in particular the 5'-RACE method [Frohman, M. A., et al., Proc. Natl. Acad. Sci. USA, 85, 8998–9002 (1988)] is preferably employed. The primers to be used in employing such PCR method can be appropriately designed based on the sequence information of the gene of the present invention as already revealed by the present invention and they can be synthesized by a conventional method.

The DNA/RNA fragment amplified can be isolated and purified by a conventional method as mentioned above, for example by gel electrophoresis.

The base sequence of the thus-obtained gene of the present invention or various DNA fragments can be determined by a conventional method, for example the dideoxy method [Proc. Natl. Acad. Sci. USA, 74, 5463–5467 (1977)] or the Maxam-Gilbert method [Methods in Enzymology, 65, 499 (1980)]. Such base sequence determination can be readily performed using a commercially available sequencing kit as well.

When the gene of the present invention is used and conventional techniques of recombinant DNA technology [e.g. Science, 224, p. 1431 (1984); Biochem. Biophys. Res. Comm., 130, p. 692 (1985); Proc. Natl. Acad. Sci. USA., 80, p. 5990 (1983); and the references cited above] are followed, a recombinant GRP17 protein can be obtained.

More detailedly, said GRP17 protein can be produced by constructing a recombinant DNA enabling the gene of the present invention to be expressed in host cells, introducing it into host cells for transformation thereof and cultivating the resulting transformant.

In that case, the host cells may be eukaryotic or prokaryotic. The eukaryotic cells include vertebrate cells, yeast cells and so on, and the vertebrate cells include, but are not limited to, simian cells named COS cells [Cell, 23, 175–182 (1981)], Chinese hamster ovary cells and a dihydrofolate reductase-deficient cell line derived therefrom [Proc. Natl. Acad. Sci. USA, 77, 4216–4220 (1980)] and the like, which are frequently used.

As regards the expression vector to be used with vertebrate cells, an expression vector having a promoter located upstream from the gene to be expressed, RNA splicing sites, a polyadenylation site and a transcription termination sequence can be generally used. This may further have an origin of replication as necessary. As an example of said expression vector, there may be mentioned pSV2dhfr [Mol. Cell. Biol., 1, 854 (1981)], which has the SV40 early promoter. As for the eukaryotic microorganisms, yeasts are generally and frequently used and, among them, yeasts of the genus Saccharomyces can be used with advantage. As regards the expression vector for use with said yeasts and other eukaryotic microorganisms, pAM82 [Proc. Natl. Acad. Sci. USA, 80, 1–5 (1983)], which has the acid phosphatase gene promoter, for instance, can be used.

Furthermore, a prokaryotic gene fused vector can be used as the expression vector for the gene of the present invention. As specific examples of such vector, there may be mentioned pGEX-2TK and pGEX-4T-2 which have a GST domain (derived from *S. japonicum*) with a molecular weight of 26,000.

*Escherichia coli* and *Bacillus subtilis* are generally and preferably used as prokaryotic hosts. When these are used as hosts in the practice of the present invention, an expression plasmid derived from a plasmid vector capable of replicating in said host organisms and provided, in this vector, for enabling the expression of the gene of the present invention, with a promoter and the SD (Shine and Dalgarno) sequence upstream from said gene and further with an initiation codon (e.g. ATG) necessary for the initiation of protein synthesis is preferably used. The *Escherichia coli* strain K12, among others, is preferably used as the host *Escherichia coli,* and pBR322 and modified vectors derived therefrom are generally and preferably used as the vector, while various known strains and vectors can also be used. Examples of the promoter which can be used are the tryptophan (trp) promoter, lpp promoter, lac promoter and PL/PR promoter.

The thus-obtained desired recombinant DNA can be introduced into host cells for transformation by using various general methods. The transformant obtained can be cultivated by a conventional method and the cultivation results in expression and production of the desired GRP17 protein encoded by the gene of the present invention. The medium to be used for the cultivation can suitably be selected from among various media in conventional use according to the host cells employed. The host cells can be cultivated under conditions suited for the growth thereof.

In the above manner, the desired recombinant GRP17 protein is expressed and produced and accumulated or secreted within the transformant cells or extracellularly or on the cell membrane.

The recombinant GRP17 protein can be isolated and purified as desired by various separation procedures utilizing the physical, chemical and other properties thereof (cf. e.g. "Seikagaku (Biochemistry) Data Book II", pages 1175–1259, 1st Edition, 1st Printing, published Jun. 23, 1980 by Tokyo Kagaku Dojin; Biochemistry, 25 (25), 8274–8277 (1986); Eur. J. Biochem., 163, 313–321 (1987)]. Specifically, said procedures include, among others, ordinary reconstitution treatment, treatment with a protein precipitating agent (salting out), centrifugation, osmotic shock treatment, sonication, ultrafiltration, various liquid chromatography techniques such as molecular sieve chromatography (gel filtration), adsorption chromatography, ion exchange chromatography, affinity chromatography and high-performance liquid chromatography (HPLC), dialysis and combinations of these. Among them, affinity chromatography utilizing a column with the GRP17 protein bound thereto is particularly preferred.

Furthermore, on the basis of the sequence information about the gene of the present invention as revealed by the present invention, for example by utilizing part or the whole of said gene, it is possible to detect the expression of the gene of the present invention in various human tissues. This can be performed by a conventional method, for example by RNA amplification by RT-PCR (reverse transcribed-polymerase chain reaction) [Kawasaki, E. S., et al., Amplification of RNA, in PCR Protocol, A guide to methods and applications, Academic Press, Inc., San Diego, 21–27 (1991)], or by Northern blotting analysis [Molecular Cloning, Cold Spring Harbor Labo 1989)], with good results.

The primers to be used in employing the above-mentioned PCR method are not limited to any particular ones provided that they are specific to the gene of the present invention and enable the gene of the present invention alone to be specifically amplified. They can be designed or selected appropriately based on the gene information provided by the present invention. Generally, they can have a partial sequence comprising about 20 to 30 nucleotides according to the established practice. Suitable examples thereof are as shown later herein in an example.

Thus, the present invention also provides primers and/or probes useful in specifically detecting such GRP17 gene.

By using the novel GRP17 gene provided by the present invention, it is possible to detect the expression of said gene in various tissues and produce the human GRP17 protein by the technology of genetic engineering and, through these, it becomes possible to analyze the human GRP17 system and function thereof deepdly involved in cell growth control, diagnose various diseases in which it is involved, for example malignant tumor, malformation and autoimmune diseases, and, further, screen out and evaluate drugs for the treatment and prevention of such diseases.

The invention will be described below with reference to examples.

In the examples, the accompanying drawings are referred to, wherein:

BRIEF DESCRIPTION OF THE DRAWINGS

FIG. 1 shows a comparison among the deduced amino acid sequence of GRP17 of the present invention (SEQ ID NO:1) and the amino acid sequences of human gadd45 (SEQ ID NO:5) and murine MyD118 (SEQ ID NO:6).

EXAMPLE 1

(1) Cloning and DNA sequencing mRNAs extracted from human tissues, namely fetal brain, adult blood vessels and placenta, were purchased from Clontech and used as starting materials.

cDNA was synthesized from each mRNA and inserted into the vector λZAPII (Stratagene) to thereby construct a cDNA library (Otsuka GEN Research Institute, Otsuka Pharmaceutical Co., Ltd.)

Human gene-containing *Escherichia coli* colonies were allowed to form on agar medium by the in vivo excision technique [Short, J. M., et al., Nucleic Acids Res., 16, 7583–7600 (1988)]. Colonies were picked up at random and human gene-containing *Escherichia coli* clones were registered on 96-well micro plates. The clones registered were stored at −80° C.

Each of the clones registered was cultured in 1.5 ml of LB medium for 24 hours, and DNA was extracted and purified using a model PI-100 automatic plasmid extractor (Kurabo). Contaminant *Escherichia coli* RNA was decomposed and removed by RNase treatment.

The DNA was dissolved to a final volume of 30 $\mu$l. A 2-$\mu$l portion was used for roughly checking the DNA size and quantity using a minigel, a 7-μl portion was used for sequencing reactions and the remaining 21-μl portion was stored as plasmid DNA at 4° C. This method, after slight changes in program, enables extraction of the cosmid, which is useful also as a probe for FISH (fluorescence in situ hybridization), which is shown later herein.

Then, the dideoxy terminator method of Sanger et al. [Sanger, F., et al., Proc. Natl. Acad. Sci. USA, 74, 5463–5467 (1977)] using T3, T7 or a synthetic oligonucleotide primer or the cycle suqencing method [Carothers, A. M., et al., Bio. Techniques, 7, 494–499 (1989)] comprising the dideoxy terminator method plus PCR method was carried out. These are methods of terminating the extension reaction specifically to the four bases using a small amount of plasmid DNA (about 0.1 to 0.5 μg) as a template.

The sequencing primers used were FITC (fluorescein isothiocyanate)-labeled ones. Generally, about 25 cycles of amplification were performed using Taq polymerase. The PCR products were separated on a polyacrylamide urea gel and the fluorescence-labeled DNA fragments were submitted to an automatic DNA sequencer (ALF™ DNA Sequencer; Pharmacia) for determining the sequence of about 400 bases from the 5' terminus side of cDNA.

Since the 3' nontranslational region is high in heterogeneity for each gene and therefore suited for discriminating individual genes from one another, sequencing was performed on the 3' side as well depending on the situation.

The vast sum of nucleotide sequence information obtained from the DNA sequencer was transferred to a 64-bit DEC 3400 computer for homology analysis by the computer. In the homology analysis, a data base (GenBank, EMBL) was used for searching according to the FASTA program of UWGCG [Pearson, W. R. and Lipman, D. J., Proc. Natl. Acad. Sci. USA, 85, 2444–2448 (1988)].

As a result of arbitrary selection by the above method, a 1.1 kilobase cDNA clone designated as GEN-554H06 was obtained from the human placenta cDNA library, and the amino acid sequence encoded by said cDNA clone was found to show high degrees of homology with the human gadd45 and murine MyD118.

To confirm its putative open reading frame, the present inventors determined the entire coding sequence and the 5' and 3' flanking sequences (1,036 nucleotides in total).

The nucleotide sequence of the cDNA clone designated as GEN-554H06 is shown in SEQ ID NO:3, the nucleotide sequence of the coding region of said clone in SEQ ID NO:2, and the putative amino acid sequence encoded by said nucleotide sequence in SEQ ID NO:1.

This cDNA comprises 1,036 bases and contains an open reading frame comprising 477 bases encoding 159 amino acid residues. The transcription start codon assumed as the first ATG in said cDNA clone was located at the 84th to 86th positions. The sequence ACTATGA (bases Nos. 81–87 in the nucleotide sequence shown in SEQ ID NO:3) was different from the consensus sequence in the vicinity of the translation initiation codon, namely (A/G)CCATGG [Kozak, M., Nucl. Acids Res., 15, 8125–8148 (1987)]. However, its high sequence homology with human gadd45 on the nucleotide level strongly suggested that said ATG at bases Nos. 84–86 was the start codon. As shown at bases Nos. 1020–1025, a polyadenylation signal was found 17 bases ahead of the poly(A) start site. Furthermore, an in-frame termination codon was located at bases Nos. 561–563. The isoelectric point (pI value) of the encoded protein was calculated at about 4.06, hence said protein was supposed to be an acidic protein.

Since the amino acid sequence encoded by this gene is highly homologous to gadd45 and MyD118, the present inventors named this gene GRP17 (gadd45 and MyD118 related protein, 17 KD) gene.

(2) Similarity of GRP17 to human gadd45 and murine MyD118

Comparison by multiple alignment of GRP17, human gadd45 and murine MyD118 is shown in FIG. 1. In the figure, identical amino acid residues are shaded. Murine MyD118 is abbreviated as "mMyD".

As shown in FIG. 1, GRP17 showed striking homology with human gadd45 and murine MyD118 on the amino acid level. Thus, on the amino acid level, GRP17 is about 55% identical with human gadd45 and about 52% identical with murine MyD118, and these presumably are family genes with an evolutionally close relation. Although known motifs were not identical, the region of amino acids Nos. 40–69 of the deduced GRP17 protein was conserved very well among these three proteins.

Gadd45 and MyD118 code for acidic proteins similarly characterized by containing a large number of acidic amino acid residues. Furthermore, these two genes have a growth inhibiting function and synergistically suppress cell growth. However, the mechanism of growth suppression is not well known as yet [Zhan, Q., et al., Mol. Cell. Biol., 14, 2361–2371 (1994)].

The sequence of GRP17 has a significant similarity to gadd45 and to MyD118 and encodes an acidic protein. These data suggest that GRP17 is a novel member of the gene family encoding acidic proteins involved in cell growth control.

The present inventors have confirmed, by isolating another human homolog of murine MyD118, that GRP17 is not the counterpart of murine MyD118. Therefore, GRP17 is presumably a novel family gene.

(3) Northern blot analysis

The expression of the GRP17 mRNA in normal human tissues was evaluated by Northern blotting using, as a probe, the human cDNA clone labeled by the random oligonucleotide priming method.

The Northern blot analysis was carried out with a human MTN blot (Human Multiple Tissue Northern blot; Clontech, Palo Alto, Calif., USA) according to the manufacturer's protocol.

Thus, the PCR amplification product from the above GEN-554H06 cDNA clone was labeled with [$^{32}$P]-dCTP (random-primed DNA labeling kit, Boehringer-Mannheim), for use as a probe.

For blotting, after 6 hours of prehybridization, hybridization was performed in a solution comprising 50% formamide/5×SSC/10×Denhardt's solution/2% SDS (containing 100 μg/ml denatured salmon sperm DNA) at 42° C. for 17 hours. After washing with 2×SSC/0.05% SDS at room temperature for 10 minutes, the membrane filter was further washed with 0.1×SSC/0.01% SDS at 65° C. for 30 minutes. An X ray film (Kodak) was exposed to the filter at −80° C. for 7 hours.

Sixteen human tissues, namely human heart, brain, placenta, lung, liver, skeletal muscle, kidney, pancreas, spleen, thyroid gland, prostate, testis, ovary, small intestine, large intestine and peripheral blood leukocyte, were examined for expression of GRP17 and, as a result, a 1.35 Kb transcript was detected in heart, placenta, liver, skeletal muscle, prostate, testis and ovary. Furthermore, upon over exposure (17 hours), the 1.35 Kb transcript was also found in lung, pancreas, small intestine and large intestine.

Northern blot analysis revealed that the expression of GRP17 is tissue-specific in normal adult tissues. In addition, a 1.7 Kb transcript was found expressed in liver alone.

Expression of these transcripts differing in size may be due to alternative splicing or to cross hybridization with another homologous gene. The strong expression of GRP17 in muscular tissues, testis and ovary is of great interest and these data may suggest that GRP17 plays an important role in the proliferation and differentiation of these tissues.

(4) Chromosomal localization by direct R-banding FISH

For isolating cosmid clones corresponding to the GRP17 cDNA, 153,600 cosmid clones were screened. In the first step of PCR screening, the first denaturation was carried out using two primers, COS1 and COS2 shown below in Table 1, at 94° C. for 1 minute, then amplification was continued with 35 cycles of 94° C. for 30 seconds, 55° C. for 45 seconds and 72° C. for 45 seconds. Thus, the number of clones was reduced to 1,440.

TABLE 1

| Primer | Base sequence |
| --- | --- |
| COS1 | 5'-TAGGCTAGGACGTTGCCTCA-3'SEQ ID NO: 7 |
| COS2 | 5'-GCTTCAACAGCAGCATCCTT-3'SEQ ID NO: 8 |

Nylon membranes dotted with the above 1,440 clones were subjected to hybridization using the cDNA as a probe under the same conditions as in Northern blotting, and independent cosmid clones were isolated.

Three independent clones obtained by the above method were each used as a probe for mapping by direct R-banding fluorescence in situ hybridization (FISH), which is based on FISH combined with prometaphase R-band chromosome samples [Takahashi, E., et al., Hum. Genet., 86, 14–16 (1990); Takahashi, E., et al., Hum. Genet., 88, 119–121 (1991)].

For suppressing the repetitive sequences contained in these clones, human Cot-1 DNA (BRL) was used according to the method described by Lichter [Lichter, P., et al., Proc. Natl. Acad. Sci. USA, 87, 6634–6638 (1990)] with slight modifications, namely using human Cot-1 DNA (BRL) in 10-fold excess. Labeling, hybridization, rinsing and detection were performed in a routine manner. Provia 100 films (Fuji ISO 100; Fuji Photo Film) were used for photomicrography (filter combination, Nikon B-2A).

As a result, after observation of 100 typical R-banded chromosome plates, signals of the three independent clones were localized to q22.1–q22.2 band of chromosome 9.

According to Holmquist [Holmquist, G. P., Am. J. Hum. Genet., 51, 17–37 (1992)], R-positive bands are GC-rich and contain tissue-specific genes and genes essential to cells. The fact that GRP17 is located in an R-positive band and is a tissue-specific gene as revealed by Northern analysis supports this notion.

We claim:

1. An isolated GRP17 gene which comprises a nucleotide sequence coding for the amino acid sequence of SEQ ID NO:1.

2. An isolated GRP17 gene which comprises the nucleotide sequence of SEQ ID NO:2.

3. An isolated GRP17 gene as defined in claim 2 which has the nucleotide sequence of SEQ ID NO:3.

* * * * *